Figure 1:
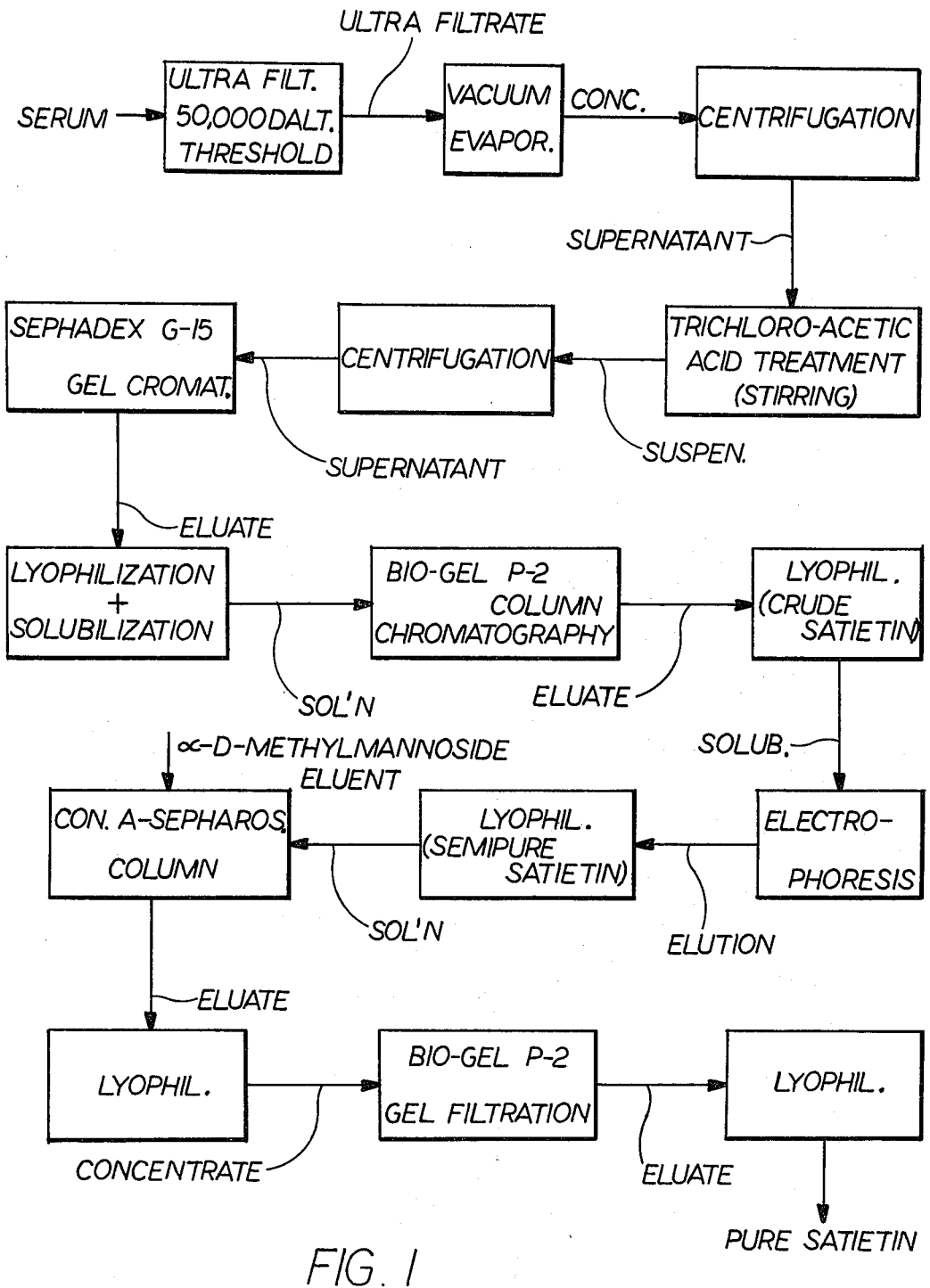

United States Patent [19]

Knoll et al.

[11] 4,430,264

[45] Feb. 7, 1984

[54] PROCESS FOR THE PREPARATION OF A SELECTIVE ANOREXOGENIC SUBSTANCE REGULATING FOOD INTAKE

[75] Inventors: József Knoll, Budapest; Janos Nagy, Szentendre, both of Hungary

[73] Assignee: Richter Gedeon Vegyészeti Gyár Rt., Budapest, Hungary

[21] Appl. No.: 425,867

[22] Filed: Sep. 28, 1982

[30] Foreign Application Priority Data

Sep. 28, 1981 [HU] Hungary ............................. 2783/81

[51] Int. Cl.³ .......................... A23J 1/06; A23K 1/04; C07G 7/00
[52] U.S. Cl. ................................ 260/112 R; 424/101; 424/177
[58] Field of Search ..................... 260/112 R; 424/101

[56] References Cited

U.S. PATENT DOCUMENTS 4,294,825 10/1981 Knoll et al. ......................... 260/112

OTHER PUBLICATIONS

Physiology & Behavior, vol. 23, pp. 497-502, Sep. 1979, Knoll.
Chem. Abstracts, vol. 91, 208025y, Knoll.

Primary Examiner—Howard E. Schain
Attorney, Agent, or Firm—Karl F. Ross; Herbert Dubno

[57] ABSTRACT

A process is disclosed for the preparation of an endogenous anorexogenic substance obtained from blood serum. The anorexogenic substance itself is also described having a specific activity of 100 units/mg.

3 Claims, 2 Drawing Figures

PROCESS FOR THE PREPARATION OF A SELECTIVE ANOREXOGENIC SUBSTANCE REGULATING FOOD INTAKE

BACKGROUND OF THE INVENTION

In No. RI-683 Hungarian patent application (U.S. Pat. No. 4,294,825) we have expounded a process for the production of an anorexogenic substance having specific effect on the central regulation of food intake. According to the procedure described in that patent, human and/or animal serum was ultrafiltered on a membrane passing molecules under 50,000 daltons (a membrane with 50,000 dalton cutoff), the ultrafiltrate was taken into dryness, redissolved in water and the solution was chromatographed on a gel column having the void volume at 50,000 daltons. The column was eluted with an aqueous solution of 0.1–1.0% sodium chloride and the fractions containing biological activity were evaporated and the residue was dissolved in water and again chromatographed on a gel column which had 50,000 daltons void volume.

Fractionation was carried out with water and the biologically active fractions were evaporated. In this way we succeeded to separate an active glycoprotein fraction which contained amino acids at an average of 60%, and carbohydrate components at an average of 10% after acid hydrolysis. The intact molecule showed specific activity on the central regulation system of food intake and did not behave as a depressive agent nor did it stimulate the central nervous system.

DESCRIPTION OF THE INVENTION

Elaborating this invention it was found that the active fraction can be further separated by the procedure described below and a new product obtained which is 3 to 4 times more effective than the previously purified one; the chemical composition of the new product essentially differs from the active fraction described and prepared earlier and it can be characterized as a pure homogeneous substance with well defined chemical composition.

We have found that a considerable part of the peptide content of the earlier purified active fraction is not covalently linked to the substance which is responsible for the biological activity and exists as indifferent components which can be eliminated by proper protein precipitation methods; at the same time the still retained small peptide-like molecules and others can completely be removed partly by electrophoresis and partly by affinity chomatography, and the pure chemically substance may be obtained this way.

According to the invention, the new substance which has an activity which is a multiple of that of the previously prepared fraction and affects selectively the satiety center, is chemically homogeneous, i.e. the pure satietin can be extracted from the human or animal serum in the following way:

Human and/or mammalian serum is filtered through a membrane with 50,000 dalton cutoff, the ultrafiltrate is then concentrated and the insoluble fraction is removed by centrifuging (advisable), then to the supernatant 5–25% (w/v), preferably 10–12% (w/v), trichloroacetic acid is added keeping the temperature between 0°–10° C., the precipitated proteins advantageously being, removed by centrifuging. The supernatant obtained is chromatographed on a gel having a void volume under 4000 daltons with a solution of 0.5–1.0% sodium chloride or with pH 6.0–7.0 buffer. The biologically active fractions were concentrated by lyophilization and subjected to chromatography on another gel column with void volume of 3000 daltons, fractionated by using distilled water and the crude product obtained in this way was further purified by electrophoresis and the pure material was isolated by means of affinity chromatography.

According to the process of this invention the execution of the first purification step, ultrafiltration, is carried out on Amnicon UM-10 membrane or on Sartorius membrane, for example, preferably under 3 at pressure and with constant stirring. The filtrate was concentrated by vacuum evaporation and the insolubles removed by centrifuging. The turbid, but precipitate free solution was brought to between 0°–10° C. and trichloroacetic acid added till the trichloroacetic acid concentration of the mixture reached 5% (w/v)–25% (w/v), preferably around 10% (w/v). Then the suspension was kept between 0°–5° C. at least for 1 h (preferably overnight) then the precipitated proteins were removed by ultracentrifugation at the same temperature when optically clear yellow supernatant was obtained. The trichloroacetic acid treatment removes all the high molecular weight serum proteins including serum albumin. Satietin containing high amount of carbohydrate, nevertheless, is not precipitated but remains insoluble in the solution in contrary to some amount of protein are still existing. It follows that this protein content already is covalently bound to the carbohydrate part in the satietin molecule.

Preparative gel chromatography was applied as the next purification step on a gel column with a void volume of 4000 daltons. This purification is preferably done on Sephadex G-15, G-10 or G-25 columns. 0.1 M ammonium acetate, pH 6.6 buffer was used as eluent, since according to the experiments this buffer assured the separation of satietin active fractions with best efficiency and a practically salt free product could be prepared by means of this volatile buffer. For the chromatography it is advisable to use 0.9% physiological sodium chloride solution, or different phosphate buffers can also be applied in pH range of 6.0–7.0. The active fraction is excluded from the gel column at the void volume ($V_o$) where $K_d=0$; $K_d$: distribution coefficient of chromatographed substances; this means that the molecular size of the product is larger than the inner holes of the gel particle so they are excluded from the gel and appeared with the eluent at ⅓ volume of the gel column. In case of Sephadex G-15 gel the molecules which are larger than 1500 daltons behave like this. The smaller molecules from the serum, on the other hand, penetrate the gel and are retarded (this being the case where $K_d>0$). Because the amount of small molecules and salts are incomparably higher than the separated satietin content in the serum, it clearly indicates that the purification rate is probably several hundred fold compared to the amount of satietin active material to the other small molecules and salts in the solute which are being retarded on the column. The trichloroacetic acid, used for protein denaturation, as a small molecule is also retarded on the gel column and so salt and acid free active substance is obtained at the void volume ⅓ of the total volume of the gel column. These fractions were pooled and concentrated by lyophilization.

The next step of the purification is also gel chromatography which is carried out, however, on a 3000 daltons void volume gel, practically on Bio-Gel P-2 column in distilled water. As a result of this step the still remaining salts and other small molecular weight fragments are removed. The fractions having satietin activity are also excluded from the gel column, and appeared at an elution volume of ⅓ the gel column volume. The active material is obtained after pooling and freeze drying of the fractions and obtained as light yellow or white powder. In this way 8–10 mg lyophilized product is obtained from 1000 ml (⅔ liter ultrafiltrate) human serum. Satietin purified by the above described method can be considered as standard crude material which, however, can be used for practical purposes as anorexogenic substance in this pure enough form, its satietin activity is as much as 25–50 units/mg.

The satietin activity of the product is measured by a bioassay worked out by us: 1 unit is equivalent to the anorexogenic activity of the amount of a satietin sample which, when given intracerebroventricularly, decreases the chow pellets consumption of rats deprived of food for 96 hours, during the first day of feeding, from 24.04±0.76 g to 10 g.

The crude satietin, which is produced according to this procedure described in this invention, can be obtained from the sera of different animals, as cattle, horse, rabbit, rat as well, although the yield and activity of the products obtained can be different i.g. from bovine serum 10–13 mg of crude material can be extracted from 1 liter serum with the activity as the human product, the specificity of the active substance of different sources was alike.

By the help of above described method 25–50 units/mg activity crude product showed an apparent molecular weight of 50,000–70,000 daltons, was a salt free substance which practically does not contain albumin and had a low protein content (5–25%) and high (60–90%) carbohydrate content in lyophilized yellow-white powder which carbohydrate part consists of four hexoses, fructose, mannose, galactose and glucose.

A considerable amount of glucoseamine could be detected in every case in the product after acid hydrolysis. Analyzing the product 4–6 protein stained bands (components or subunits) could be detected by means of SDS gel electrophoresis and analytical isoelectric focusing. By the use of high-voltage electrophoresis the product also proved to be still complex at pH 6.2 and 1.6 buffer systems. The biologically active major component does not move or only slightly moves from the start in the direction of the negative pole. The active components were detectable by ninhydrin or periodic acid-Schiff staining simultaneously indicating the glycoprotein nature of the material.

The crude satietin obtained by the above mentioned method can be further purified by electrophoretic methods, practically with paper electrophoresis under laboratory conditions. In the course of the paper electrophoresis separation in pH 6.2 buffer, the major product ($R_f=0.1$) can be separated with 75% yield, while the other glycopeptide-like components were moved towards the positive pole, thus the procedure resulted in highly active substance identically stained with ninhydrin and periodic acid-Schiff reagent was nicely separated. (60–100 unit/mg)

The separated active material is already a highly purified product, according to the previously used methods; for example it seems to be homogeneous by gel chromatography of gradient polyacrylamide gel electrophoresis, with nearly 100 unit/mg activity, and essentially a glycoprotein-like material, which, however, as the composition and activity values fluctuate, cannot be considered a chemically homogeneous, standard substance. In our further studies we tried to isolate a pure homogeneous material in every respect and we have found that this problem can be solved if the active substance is submitted to a further purification step namely affinity chromatography (which is a newly developed technique for separation of glycoproteins, e.g. D. H. Swallow, L. Evans, D. A. Hopkinson: Nature 269, 261–262; 1977).

For this step a sorbent is needed which is capable of binding specifically a group of substances to be separated; since satietin is a glycoprotein and contained covalently linked carbohydrate moiety we apply an adsorbent which shows specific affinity for the glucopyranose groups of satietin. Of this group of specific adsorbents, especially the Con A-Sepharose gel proved to be convenient for tis purpose. This adsorbent-gel is Sepharose 4 B activated by cyanbromide to which Concavalin A is coupled, and which specifically binds the alpha-D-Mannopyranosyl- or alpha-D-glucopyranosyl groups while the other substances (proteins, peptides, etc) not containing these groups will be excluded from the gel. These excluded substances appeared at the void volume in the course of the elution, at ⅓ volume of the total volume of the gel column, while the bound glycoprotein-like substances on the gel in some cases can be further separated depending on the chemical nature of the compounds particularly if gradient elution is used.

According to this step of the invention, in the practical work of affinity chromatography the earlier purified satietin product is dissolved in a neutral starting buffer. 0.02 M Tris-hydrochloride (2-amino-2-hydroxymethyl-1,3-propanediol-hydrochloride) is preferably used as a starting buffer which contains 0.5–1.0 M sodium chloride and the mixture should also contain $Mn^{2+}$ and $Ca^{2+}$ ions (1 mM). The high concentration of sodium chloride is required in the starting buffer in order to prevent nonspecific protein-binding between the adsorbent and the proteins present in the solute. The dissolved substance in the starting buffer is then chromatographed on the Con A-Sepharose column which was equilibrated with the starting buffer, by 10 column volumes washing at least with the starting buffer.

Figure 2:
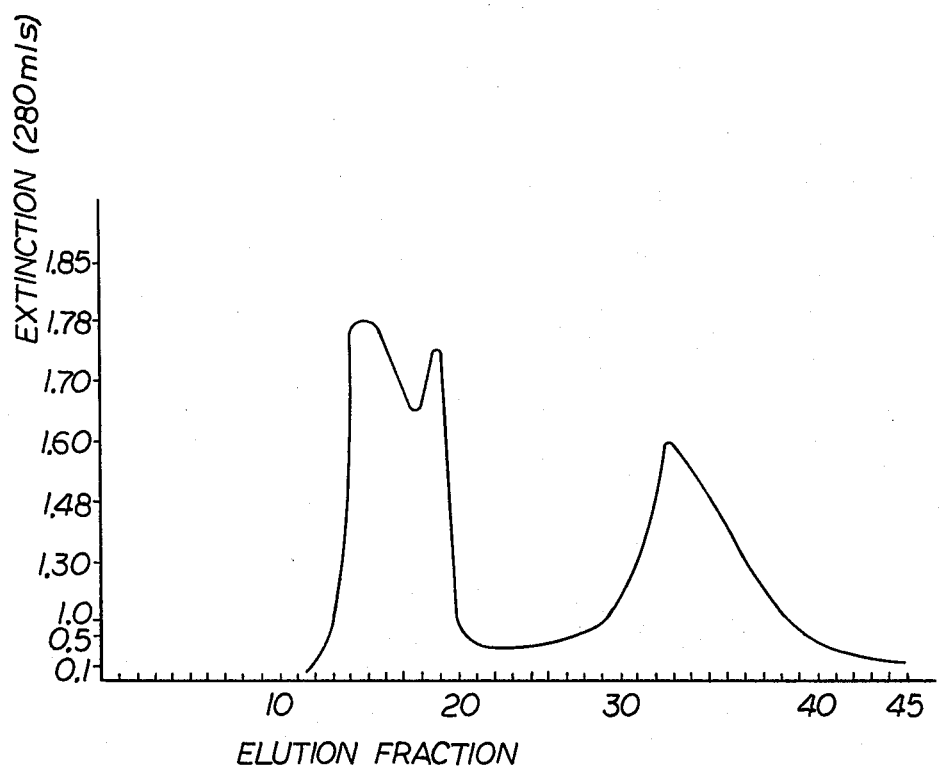

After feeding the column with the satietin product to be purified the elution was carried out with the starting buffer containing alpha-D-methylmannoside in increasing concentrations. Practically, 0.5 M concentration of alpha-methylmannoside solution is poured in drops continuously into the eluent (starting buffer) and the linear gradient is formed by keeping the mixture constantly stirring. The alpha-methylmannoside concentration of the eluent thus increases linearly during the elution; the ion concentration and pH value are not changed during the elution. If the elution process is followed by UV spectrophotometer at 254 or 280 nm, then an elution diagram is obtained. FIG. 2 shows the elution profile, where the unretarded component A excluded from the column and appeared at the void volume, whereas bound component B is retarded with higher retention value and has an approximately symmetrical peak as a result of the increasing concentration of alpha-methylmannoside. In this way the biolgically active substance is obtained by pooling and concentrating the appropriate fractions eluted from the column. Since the substance still contains salts and alpha-methylmannoside originated from the buffer it needs a further desalting procedure which is carried out by gel chromatography. This step is performed on a gel column with 3000 daltons void volume, advantageously on Bio-Gel P-2 gel with deionized water. In the course of this gel-chromatographic step the salts and other small molecules because of their molecular size are going inside the gel particles and retarding, the pure satietin, however, is excluded from the gel and appears with ⅓ volume of the total volume of the column. The active fractions obtained by the elution of deionized water are pooled and freeze dried; the pure, homogeneous active satietin is obtained as white powder.

The complete isolation procedure of satietin active substance from human or animal serum is outlined in FIG. 1. 1.5 mg active satietin can be extracted from 1 liter human serum, the specific activity of this substance was found to be 100 units/mg.

The molecular weight of pure satietin isolated according to the invention was estimated by SDS-gel electrophoresis and showed an appearent molecular weight of 60,000–70,000 daltons, When the sample was examined by isoelectric focusing in polyacrylamide gel in the presence of ampholines with pH range of 5–7 and 7–9 we found that it exists in two distinct isoelectric forms in the pI range of 7.00–7.05 providing further support that the isolated glycoprotein was homogeneous. The analysis of product after acid hydrolysis showed the next composition:

| protein content | 15% |
| carbohydrate content | 75% |
| glucose amine | 4% |
| water | 5% |

Amino acid content:
  Asp 1.21%, Thr 0.66%, Ser 0.71%, Glu 1.87% Pro 0.45%, Gly 0.42%, Ala 1.58%, Cys 0.13% Val 0.55%, Met 0.12%, Ile 0.26%, Leu 0.90% Tyr 0.31%, Phe 0.44%, $NH_3$ 0.24%, Lys 3.79% His 0.15%, Arg 0.49%

Sugar components:
  fructose 19%, mannose 21%, galactose 11%, glucose 24%

The water content of the product vary depending upon the condition of lyophilization.

The homogeneity of satietin product isolated according to this invention is proved by the evidence of affinity chromatography, polyacrylamide gel electrophoresis in presence of sodium dodecyl sulfate (SDS), gradient gel electrophoresis in slab gel, analytical isoelectric focusing, and end group analysis by means of the dansylation technique.

The isolation procedure of this invention is illustrated by the next example:

EXAMPLE (a) 3,000 ml of human serum was processed by ultrafiltration on Amicon UM-10 membrane under 3–4 at. and constant stirring. The ultrafiltrate, about 2,000 ml, was then concentrated to 60 ml under vacuum evaporation. The mixture was centrifuged at 9,000×g for 30 min, the clear supernatant was brought to 0° C. and 0.2 volume of 55% (w/v) trichloroacetic acid was added keeping the mixture between 0°–5° C. and constant stirring during this procedure. After 1 h the suspension was centrifuged at 30,000×g for 30 min at 5° C. in order to remove the precipitated proteins. Further purification of the active material present in the completely clear supernatant was achieved by gel chromatography on a column (5.0×90 cm) of Sephadex G-15, equilibrated and eluted with 0.1 M ammonium acetate, pH 6.6 buffer. The fractions between 500–600 ml were pooled and lyophilized, dissolved in 10 ml of distilled water and applied to a column (2.5×90 cm) of Bio-Gel P-2 (100–200 mesh) and eluted with the same solvent. The fractions between 130–180 ml were pooled, lyophilized and yielded 25–30 mg of salt free crude satietin product as white powder.

(b) 30 mg of the previously purified substance was dissolved in 6 ml of distilled water, applied to Whatman No. 3M paper (1 mg loaded on the 1 cm), and subjected to high-voltage electrophoresis at a voltage gradient of 30 V/cm for 3 h at pH 6.2 (10% v/v pyridine; 0.5% v/v acetic acid). After drying the 1 cm wide paper strips were stained by ninhydrin and perjodic acid-Schiff reagents, respectively, in order to visualize the separated components. According to these double stainings four distinctive bands (Nos. 1,2,3,4) were ninhydrin positive, while only No. 1 and No. 2 were stained by periodic acid-Schiff reagent. Each band was eluted with water and lyophilized to dryness. Fractions No. 1 and No. 2 proved to be biologically active (FIG. 1) and yielded amounts 20 to 23 mg of freeze dried powder with 50–100 units/mg satietin activity. ($R_f$ values of Nos. 1 and 2 were 0.00 and −0.11, respectively; mobility relative to Phe→Lys=1.00).

(c) 20 mg of electrophoretically purified substance was dissolved in 4 ml of starting buffer (0.02 M Tris-HCl, 0.5 M NaCl, 0.001 M $MnCl_2$, and 0.001 M $CaCl_2$, pH 7.0) and subjected to a column (1.7×37 cm) of Con A-Sepharose. Elution of the bound substance was achieved by using a linear concentration gradient (0–0.5 M) of alpha-D-methylmannoside (as a result of mixing 100 ml of starting buffer and 100 ml of the same buffer containing 0.5 M alpha-D-methylmannoside under constant stirring). Elution was followed at 280 nm by using an UV monitor. The active fractions (between 75–100 ml) were pooled and concentrated to 10 ml by lyophilization.

The salt free substance separated by this procedure was obtained by simple gel filtration on Bio-Gel P-2 column (2.5×90 cm) as it was previously applied. Deionized water was used as eluent and the separated fractions (between 140–180 ml) were pooled and lyophilized. The pure satietin appeared as dried white powder in the amount of 4–5 mg. The specific activity of this substance was found to be 100 units/mg.

What we claim is:
1. A process for producing an endogenous anorexogenic substance which comprises the steps of:
  (a) ultrafiltering, through a 50,000 dalton threshold membrane, blood serum to recover an ultrafiltrate, partially evaporating said ultrafiltrate to form a first concentrate, and removing insolubles from said first concentrate;
  (b) precipitating proteins from the first concentrate following step (a) by treating it with trichloroacetic acid in an amount of substantially 5 to 25% w/v at a temperature of substantially 0° to 10° C., and separating precipitated proteins from the resulting solution;
  (c) chromatographing said solution on a gel having a void volume under substantially 4000 dalton with a solution of substantially 0.5 to 1.0% sodium chloride of phosphate buffer at a pH of substantially 6.0 to 7.0 to recover anorexogenically biologically active fractions, and concentrating said fractions by lyophilization to form a second concentrate;

(d) chromatographing said second concentrate upon a gel column with a void volume of substantially 3000 dalton to recover anorexogenically biologically active fractions;

(e) lyophilizing the biologically active fractions of step (d) to yield a crude product forming said substance; and (f) subjecting the crude product of step (e) to electrophoresis in a buffer of substantially pH 6.0 to 6.5, eluting the electrophoresed product, and lyophilizing the eluted electrophoresed product to form said substance in a semipure state.

2. The process defined in claim 1, further comprising the step of:

(g) purifying the semipure substant of step (f) by:
   ($g_1$) forming a solution of said semipure substance,
   ($g_2$) contacting said solution with a further gel column to bind said semipure substance thereto,
   ($g_3$) eluting the further gel with an eluent containing progressively increasing concentrations of alpha-D-methylmannoside to recover active fractions,
   ($g_4$) concentrating the active fractions of step ($g_3$) to form a third concentrate,
   ($g_5$) chromatographing the third concentrate upon a gel having a void volume of substantially 3000 dalton to form highly active fractions, and
   ($g_6$) lyophilizing said highly active fractions to produce said substance in a pure state.

3. The product made by the process defined in claim 1, or claim 2.

* * * * *